(12) United States Patent
Xie et al.

(10) Patent No.: US 8,194,953 B2
(45) Date of Patent: Jun. 5, 2012

(54) METHOD AND SYSTEM OF MATERIAL IDENTIFICATION USING BINOCULAR STEROSCOPIC AND MULTI-ENERGY TRANSMISSION IMAGES

(75) Inventors: Yali Xie, Beijing (CN); Qitian Miao, Beijing (CN); Hua Peng, Beijing (CN); Kejun Kang, Beijing (CN); Haifeng Hu, Beijing (CN); Zhiqiang Chen, Beijing (CN); Xueguang Cao, Beijing (CN); Chuanxiang Tang, Beijing (CN); Jianping Gu, Beijing (CN); Xuewu Wang, Beijing (CN); Hongsheng Wen, Beijing (CN); Bei He, Beijing (CN); Yaohong Liu, Beijing (CN); Shangmin Sun, Beijing (CN); Quanwei Song, Beijing (CN); Jin Lin, Beijing (CN); Xianli Ding, Beijing (CN)

(73) Assignees: Nuctech Company Limited, Beijing (CN); Tsinghua Universiy, Beijing (CN)

( * ) Notice: Subject to any disclaimer, the term of this patent is extended or adjusted under 35 U.S.C. 154(b) by 971 days.

(21) Appl. No.: 12/180,850

(22) Filed: Jul. 28, 2008

(65) Prior Publication Data
US 2009/0087026 A1 Apr. 2, 2009

(30) Foreign Application Priority Data

Aug. 2, 2007 (CN) .......................... 2007 1 0119871
Feb. 25, 2008 (CN) .......................... 2008 1 0081325

(51) Int. Cl.
*G21K 4/00* (2006.01)
*G06K 9/46* (2006.01)
(52) U.S. Cl. ......................................... 382/128; 378/41

(58) Field of Classification Search .................. 382/128; 378/41
See application file for complete search history.

(56) References Cited

U.S. PATENT DOCUMENTS

| 5,524,133 A | 6/1996 | Neale et al. ..................... 378/53 |
| 6,018,562 A | 1/2000 | Willson ........................... 378/9 |
| 2003/0081720 A1 | 5/2003 | Swift et al. ..................... 378/41 |
| 2004/0101087 A1 | 5/2004 | Hsieh et al. ....................... 378/4 |

FOREIGN PATENT DOCUMENTS

CN 2529247 Y 1/2003
(Continued)

OTHER PUBLICATIONS

Wang et al ("Stereoscopic dual-energy X-ray imaging for target materials identification", IEE Proceedings—Vision, Image, and Signal Processing, vol. 150 No. 2, Apr. 2003).*

(Continued)

*Primary Examiner* — Clayton E Laballe
*Assistant Examiner* — Leon W Rhodes
(74) *Attorney, Agent, or Firm* — Westman, Champlin & Kelly, P.A.

(57) ABSTRACT

The present invention provides a method and system of material identification using binocular steroscopic and multi-energy transmission image. With the method, any obstacle that dominates the ray absorption can be peeled off from the objects that overlap in the direction of a ray beam. The object that is unobvious due to a relatively small amount of ray absorption will thus stand out, and the material property of the object, such as organic, mixture, metal and the like can be identified. This method lays a fundament for automatic identification of harmful objects, such as explosive, drugs, etc., concealed in a freight container.

21 Claims, 13 Drawing Sheets

FOREIGN PATENT DOCUMENTS

| | | |
|---|---|---|
| CN | 1995993 | 7/2007 |
| CN | 101210895 A | 7/2008 |
| EP | 0 610 084 A2 | 2/1994 |
| EP | 1 938 752 A1 | 11/2007 |
| GB | 2 329 817 A | 3/1999 |
| GB | 2 390 005 | 12/2003 |
| GB | 2 433 777 A | 7/2007 |
| JP | 52132752 | 11/1977 |
| JP | 57093241 | 6/1982 |
| JP | 6116732 | 1/1986 |
| JP | 6397149 | 4/1988 |
| JP | 63168153 | 7/1988 |
| JP | 63246738 | 10/1988 |
| JP | 64002628 A | 1/1989 |
| JP | 6504838 | 6/1994 |
| JP | 07167801 | 7/1995 |
| JP | 09282443 A | 10/1997 |
| JP | 10146330 A | 6/1998 |
| JP | 11500229 | 1/1999 |
| JP | 2004174264 | 6/2004 |
| JP | 2004363109 | 12/2004 |
| JP | 2005512025 | 4/2005 |
| JP | 2005530153 | 10/2005 |
| JP | 2006212056 A | 8/2006 |
| JP | 2007-17304 A | 1/2007 |
| JP | 2007510927 | 4/2007 |
| JP | 2010511170 A | 4/2010 |
| WO | WO 2006/007723 A1 | 1/2006 |

OTHER PUBLICATIONS

"Image Segmentation for Binocular Stereoscopic Dual-Energy X-Ray Imaging", by Y.S. Yong et al., *Journal of Electronic Imaging*, vol. 14(4), Oct.-Dec. 2005, pp. 13 pgs.

"Stereoscopic Dual-Energy X-Ray Imaging for Target Materials Identification", by T.W. Wang et al., *IEEE Xplore*, 2002, pp. 122-125.

"Stereoscopic Imaging Using Folded Linear Dual-Energy X-Ray Detectors", by JPO Evans, *Meas. Sci. Technol.*, 2002, pp. 1388-1397.

"X-Ray Imaging for Security Applications", by J. Paul Evans, *Proc. Of SPIE*, vol. 5199, pp. 26-36.

"Colour 3D X-Ray Imaging for Security Screening", by J.P.O. Evans et al., *IEEE Xplore*, pp. 372-377.

Yutaka Ishiyama et al, "Stereo Correspondence Using Segment Connectivity", Journal of the Association for Information Processing, vol. 40 No. 8, Aug. 1999, p. 3219-3229.

Yutaka Ishiyama et al., "Search for Correspondence Candidates in Segment-based Stereo", The Institute of Electronics, Information and Communication Engineers, vol. 96, No. 491, p. 57-64.

Japanese Office Action from corresponding application No. JP2008-199394 issued by the Japanese Patent Office on Jan. 4, 2011.

International Search Report for PCT Application No. PCT/CN2008/001418, dated Nov. 6, 2008, 3 pgs.

English Translation for Written Opinion for PCT Application No. PCT/CN2008/001418, dated Nov. 6, 2008, 9 pgs.

First Australian Office Action for Australian Application No. 2008203434, dated Dec. 17, 2009, 4 pgs.

First Chinese Office Action (without English translation) for Chinese Application No. 200810081325.1, dated Jun. 26, 2009, 7 pgs.

Second Chinese Office Action (without English translation) for Chinese Application No. 200810081325.1, dated Jan. 8, 2010, 5 pgs.

Third Chinese Office Action (without English translation) for Chinese Application No. 200810081325.1, dated Nov. 1, 2010, 3 pgs.

First Russian Office Action (with English translation only) for Russian Application No. 2008131769, 6 pgs.

Second Japanese Office Action (without English translation) for Japanese Application No. 2008-199394, 3 pgs.

"Automated 2-D Cephalometric Analysis on X-ray Images by a Model-Based Approach;" Yue W. et al, IEEE Transactions on Biomedical Engineering, vol. 53, No. 8, Aug. 2006, pp. 1615-1623.

"Explosive Detecting Technic;" He Shan, Police Technology, No. 6, Dec. 2007, pp. 63-64 (English translation of this journal is not available).

\* cited by examiner

METHOD AND SYSTEM OF MATERIAL IDENTIFICATION USING BINOCULAR STEROSCOPIC AND MULTI-ENERGY TRANSMISSION IMAGES

BACKGROUND OF THE INVENTION

The present application claims priority of Chinese patent application Serial No. 200710119871.5, filed Aug. 2, 2007 and Chinese patent application Serial No. 200810081325.1, filed Feb. 25, 2008, the content of which is hereby incorporated by reference in its entirety.

1. Field of Invention

The present invention relates to the field of radiographic imaging technology, and in particular to a scan radiographic imaging method used in a system for radiographic examination of large-sized objects.

2. Description of Prior Art

With the help of the penetrating capability of high-energy X-rays, radiographic imaging technology can look into the inner structure of an object in a non-contact manner so as to obtain a transmission image of the object. For the examination of large objects in the prior art, the operation principle of scanning radiographic imaging is that X-rays are emitted by a radiation source, penetrate through an object to be detected, are received by a detector and then converted into electric signals to be inputted into an image acquisition system, which in turn inputs the image signals into a computer monitor for displaying the detected image. In general, a transmission image by radiographic imaging is actually the projection of every object penetrated by the beam of X-rays and contains no information about spacial depth. Therefore, a scan image will be one formed by superimposing the projection of each of the multiple objects along a scanning beam if all the objects are exactly located in the incident direction of X-rays. This is adverse to the examination of an object hidden behind the others. In order to overcome the above problem, in the field of radiographic imaging there has been proposed a relatively mature technology for object reconstruction, which utilizes computerized tomography scanning technique. Unfortunately, this technique has drawbacks of complex structure, high cost, inability to carry out a quick examination on large objects and low passing-through ratio. Further, the material of the examined object cannot be identified.

In contrast, the processing technique of binocular steroscopic radiographic transmission image is a radiographic imaging method that can separate, from an image, each object at a different depth in a detection space to remove any unwanted obstacle. This technique can be used to peel off some overlapping objects in the transmission image so that the overlaid objects appear more obvious. However, the material property of an object cannot be identified. On the other hand, the identification technique for multi-energy radiographic transmission image can identify the material property, such as organic, mixture, metal, etc., by using the fact that certain object has a varying attenuation capability with respect to different levels of energy. Unfortunately, this technique can identify only the material property of the object that dominates the attenuation absorption when the objects overlap on each other. The property of an object cannot be identified with this technique if the object absorbs only a trivial part of the overall attenuation.

SUMMARY OF THE INVENTION

In view of the above disadvantages in the prior art, the present invention provides a scan radiographic identification-imaging method for a large-sized object radiographic examination system of a simple structure. The method combines the binocular steroscopic technique with the multi-energy transmission imaging technique to identify the material property from a transmission image. The method first creates the template planes of objects along the depth direction in a detection space by means of the binocular steroscopic technique. Then, depth plane grey images of the objects are reconstructed from the transmission image. Finally, the multi-energy technique is applied to identify the materials of the objects for which the reconstruction of corresponding grey images in depth plane succeed.

According to the present invention, a material identification method using binocular steroscopic and multi-energy transmission images comprise the following steps:

causing two angled X-ray beams to penetrate through objects under examination so as to obtain data of left and right transmission images, segmenting said left and right transmission images and matching the results of said segmentation;

creating a template depth plane along the depth direction of the transmission images;

reconstructing a depth plane grey image from the transmission images;

repeating the above process on transmission images of variation energy to obtain a template depth plane of each depth plane for the variation energy;

merging the template planes for different energy levels at the same depth to obtain a template depth plane for each depth plane and energy of a predetermined group of energy levels;

identifying the material of the objects for each of which the grey reconstruction in depth plane succeeds.

With the material identification method using binocular steroscopic and multi-energy transmission images according to the present invention, any obstacle that dominates the ray absorption can be peeled off from the objects that overlap in the direction of a ray beam. The object that is unobvious due to a relatively small amount of ray absorption will thus stand out, and the material property of the object, such as organic, mixture, metal and the like can be identified.

With the method of the present invention, it is possible to identify the material of a non-dominant component along the ray direction. This lays a fundament for automatic identification of harmful objects, such as explosive, drugs, etc., concealed in a freight container.

DETAILED DESCRIPTION OF PREFERRED EMBODIMENTS

Below, a detailed description is given to the present invention with reference to the figures.

According to the present invention, the material identification method using binocular steroscopic and multi-energy transmission image comprises three sections of implementation described hereafter.

1. Obtaining a Template Depth Plane for a Binocular Steroscopic Image of Each Energy by Applying the Binocular Steroscopic Processing Technique to the Binocular Steroscopic Image, and Merging the Depth Plane Templates for Different Energy Level into a Template for a Group of Depth Plane Images.

Figure 1:
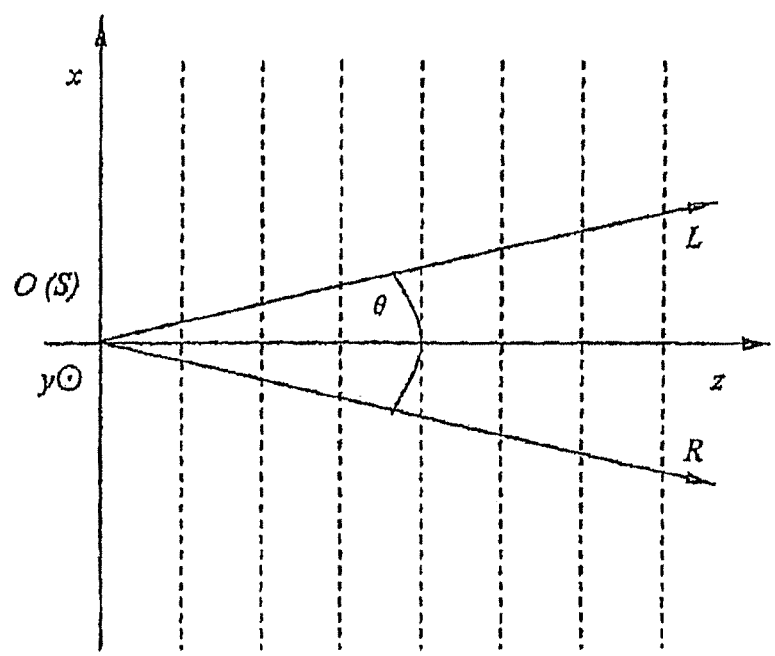
FIG. 1 shows a schematic depth plane of a detection space with the binocular steroscopic technology according to the present invention.

FIG. 1 shows a schematic depth plane of a detection space with the binocular steroscopic technology according to the present invention. As shown in FIG. 1, the detection space is a 3D space formed of a region that is scanned across by a sector defined between a ray source (origin O) and detectors (vertical arrays at positions of L and R). In this space, O represents the coordination origin, S denotes the position of the ray source, L and R represents left and right detector arrays, OL and OR denotes left and right ray beams, and θ denotes the angle between the left and right ray beams.

In FIG. 1, the scanning direction (vertically upward) is set as the positive direction of x axis, with the coordinate value being scanning number. The arrangement direction of detectors (vertically extending out from the plane of paper) is set as the positive direction of y axis, with the coordinate value being detector number. The horizontally rightward direction is set as the positive direction of z axis, with the coordinate value being depth plane number. The space, in which the orthogonal coordinate system is built and the position O of the ray source S is the origin, is called detection space. Depth planes are a series of spatial planes parallel with the x-O-y plane. The dashed lines in FIG. 1 denote the projection of the depth planes on the x-O-z plane, and the depth of each depth plane is the distance between the plane and the x-O-y plane. L and R denote the projections of the left and right ray beams on the x-O-z plane, respectively. θ denotes the angle between the projections of the left and right ray beams on the x-O-z plane.

Image edge extraction technique can be used to obtain template image of an object in the detection space, that is, several edges are firstly obtained by detecting local discontinuity and then connected with each other. Such edge extraction method is reliable in the segmentation of an X-ray transmission image due to the inherent characteristics of the X-ray transmission image for overlapping objects. In the present invention, Sobel and Canny edge detection operators are used simultaneously to extract edges, which are then synthesized into a resultant edge image. Finally, edge connection is performed on the resultant edge image so as to define enclosed regions. In this way, the segmentation for each of the left and right views can be completed.

Figure 2:
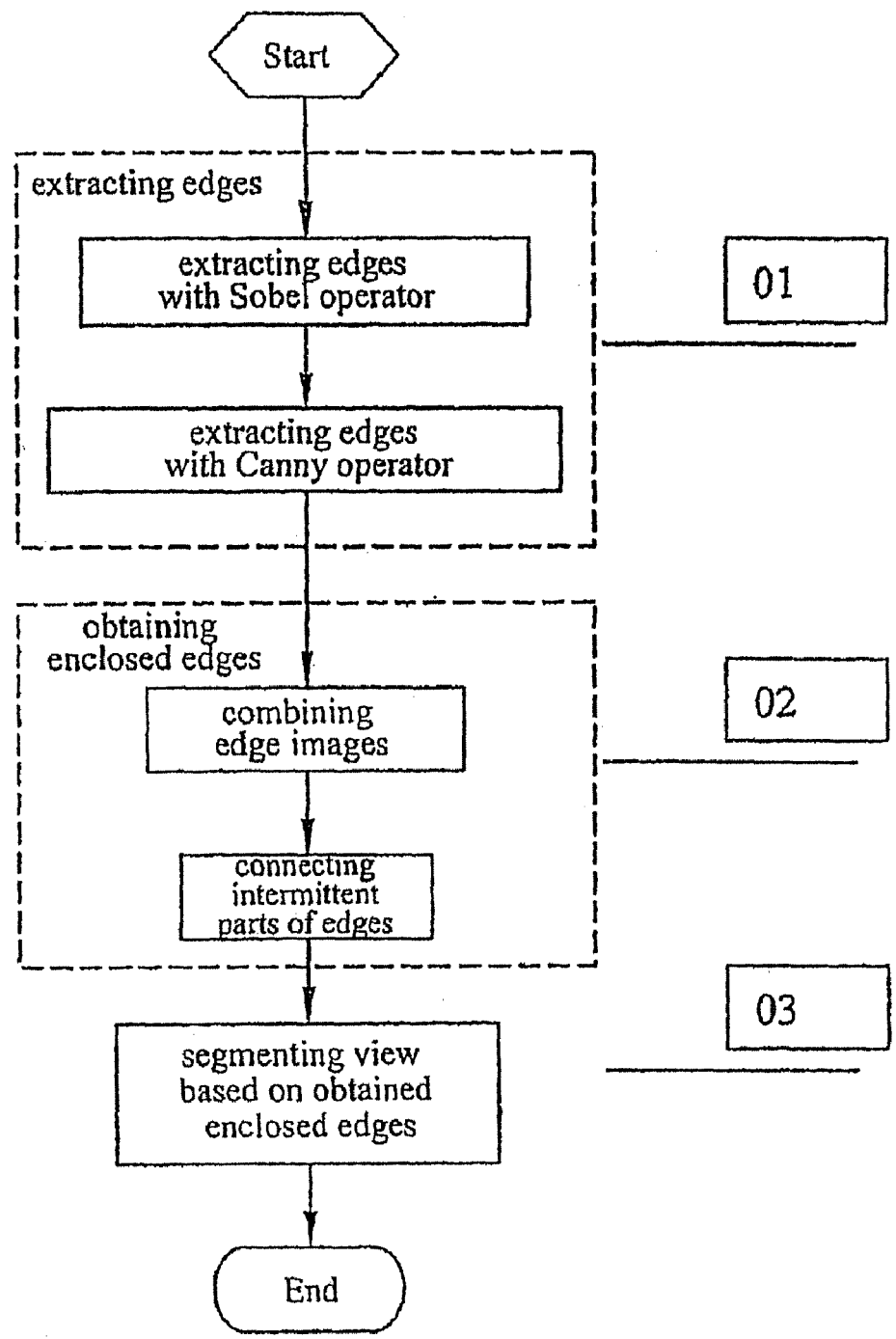
FIG. 2 shows a detailed flowchart of image segmentation according to the present invention.

FIG. 2 shows a detailed flowchart of image segmentation according to the present invention, with reference to which a specific description is given to the image segmentation in the present invention.

The flow starts with edge extraction in step 01. In the present invention, Sobel and Canny edge detection operators are used simultaneously for edge extraction. Consider a digital image $\{f(i, j)\}$, $f(i, j)$ represents the grey value of a pixel at the i-th row and the j-th column, and $\{f(i, j)\}$ represents a set of all pixels in the image. For each pixel in a digital image $\{f(i, j)\}$, Sobel edge detection operator calculates a weighted grey difference between the pixel and its neighbor (upper, lower, left and right) pixels, with the nearer neighbor pixel having a larger weight and the farther neighbor pixel having a smaller weight, as defined in the following equation:

$$s(i, j) = |\Delta_x f| + |\Delta_y f|$$
$$= |(f(i-1, j-1) + 2f(i-1, j) + f(i-1, j+1)) -$$
$$(f(i+1, j-1) + 2f(i+1, j) + f(i+1, j+1))| +$$
$$|(f(i-1, j-1) + 2f(i, j-1) + f(i+1, j-1)) -$$
$$(f(i-1, j+1) + 2f(i, j+1) + f(i+1, j+1))|$$

In the above equation, $|\Delta_x f|$, $|\Delta_y f|$ represent the convolution sums of convolution operators $\Delta_x f$, $\Delta_y f$ at the i-th row and the j-th column, respectively. The convolution operators are defined in a matrix form as $$\underbrace{\begin{pmatrix} 1 & 2 & 1 \\ 0 & 0 & 0 \\ -1 & -2 & -1 \end{pmatrix}}_{\Delta_x f}, \underbrace{\begin{pmatrix} 1 & 0 & -1 \\ 2 & 0 & -2 \\ 1 & 0 & -1 \end{pmatrix}}_{\Delta_y f}.$$

Next, a threshold Th is selected, and any pixel (i, j) will be determined as a step-type edge point if it fulfills S(i, j)>Th, where S(i, j) represents the resultant edge image.

On the other hand, Canny edge detection algorithm generally comprises steps of: smoothing the image with a Gauss filter; calculating the magnitude and direction of gradient by use of finite difference of one-order partial derivative; applying non-maximum suppression image to the magnitude of gradient; and detecting and connecting edges via a double threshold algorithm. Canny operator can reduce pseudo edges by using the double threshold algorithm. Specifically, the non-maximum suppression image is binarized with two thresholds $Th_1$ and $Th_2$, where $2Th_1 \approx Th_2$, to obtain two threshold edge images $N_1(i,j)$ and $N_2(i,j)$. $N_2(i,j)$ is extracted with the higher threshold $Th_2$ and thus has fewer pseudo edges, but there exists discontinuity in it. Therefore, it is necessary to connect each intermittent edge into an integral and continuous one in $N_2(i,j)$. The algorithm begins with a pixel referred to as an end point in $N_2(i,j)$, then searches at 8-neighborhood around a pixel in $N_1(i,j)$ corresponding to the end point for a pixel which can be connected with the end point. In this way, the algorithm continuously and repeatedly collects edge points in $N_1(i,j)$ until the intermittent edge in $N_2(i, j)$ is rendered into an uninterrupted outline.

Finally, an enclosed edge image is obtained in step 02. As will be explained later, all of the edges detected by Sobel and Canny edge detection operators should be taken into account to enable edge connection for a satisfactory closed edge image. In the present invention, the initial edge image results from a logic OR operation between the binary edge images by the above two operators. Each of the edges obtained by the foregoing method usually comprises intermittent parts or even individual edge pixels due to the effect of noise and the like, it is therefore necessary to connect these parts or edge pixels. In the present invention, two edge pixels are connected based on the similarity of them in terms of gradient magnitude and/or gradient direction. For example, a pixel (s, t) can be connected with a pixel (x, y) if the former lies in the neighborhood of the latter, and their gradient magnitudes and gradient directions meet the following requirement with respect to the given thresholds:

$$|\nabla f(x, y) - \nabla f(s, t)| \leq T$$

$$|\nabla \varphi(x, y) - \nabla \varphi(s, t)| \leq A$$

where $$\nabla f(x, y) = \begin{pmatrix} G_x \\ G_y \end{pmatrix} = \begin{pmatrix} \frac{\partial f}{\partial x} \\ \frac{\partial f}{\partial y} \end{pmatrix}, \varphi(x, y) = \arctan\left(\frac{G_x}{G_y}\right),$$

T represents the threshold for magnitude, and A for angle. As such, by repeating the above determination and connection on all relevant edge pixels, a continuous and closed edge can be acquired.

At step 03, each image of the left and right views is segmented according to a corresponding resultant enclosed edge image. Here, since the image is partitioned into two kinds of regions, i.e., inner and outer, by the closed edge, morphological dilation erosion can be employed to find a pixel belonging to one of the inner regions. Then, starting with this pixel and by use of region growing method, the pixels belonging to the inner region are filled with the value of "1", and the pixels belonging to the outer region are filled with the value of "0". As a result, the binary template for each inner region is obtained. The template has a size equal to the projection of the detection space on the x-O-y plane, i.e., the number of scanning operations (width) x the number of detectors (height). Till now, the image segmentation is completed, and thus templates for the object are obtained.

According to the present invention, the objects on the two template images are matched according to certain rule through the binocular stereoscopic technique. Specifically, for an object, its continuous region filled with the value of "1" in the left template image is compared with each of the templates in the right template image to find the corresponding template in the right view. In this way, each matched object has a corresponding template in each of the left and right views, and the positional difference between the two templates in the horizontal direction is called parallax pr.

According to the binocular steroscopic theory, the relationship between each transmission depth z and parallax pr is defined as $$\tan(\theta/2) = pr/z$$

Each of the matched objects is drawn in the depth plane template at a corresponding depth, which is $$z = pr/\tan^{-1}(\theta/2) = (\mu_{x,i} - \mu_{x,j})/\tan^{-1}(\theta/2)$$

$\mu_{x,i}$ and $\mu_{x,j}$ are the horizontal coordinates of gravity centers in the left and right views for each matched object in the depth plane template. The parallax is directly proportional to the depth of each plane.

Figure 3:
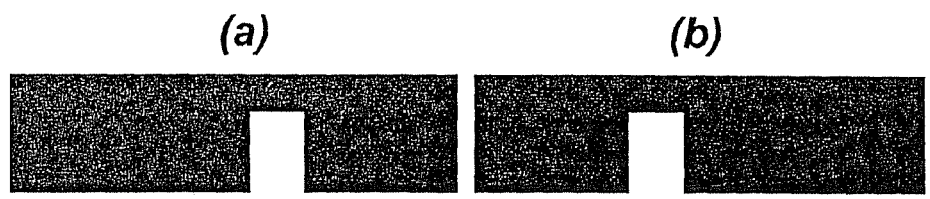
FIG. 3 shows an example of the matched template planes according to the present invention.

FIG. 3 shows an example of the matched template planes according to the present invention. As shown in FIG. 3, the segmentation results of the left and right views are shown. FIG. 3(a) is a template in the left view for an object, and FIG. 3(b) is a template in the right view for the same object. Here, the templates for the object are both rectangular.

For a depth plane template obtained from a transmission image by the binocular steroscopic technique, the plane number reflects the position of an object in the detection space along the depth direction, and the geometric shape of the template reflects the contour of the object.

The above process is repeated for each transmission image of variation energy, and the template depth plane for each plane and energy can be obtained. Thus, an template depth plane of each plane for all levels of energy can be acquired by merging the template planes of different energy levels at the same position through logic operation "OR".

Figure 4:
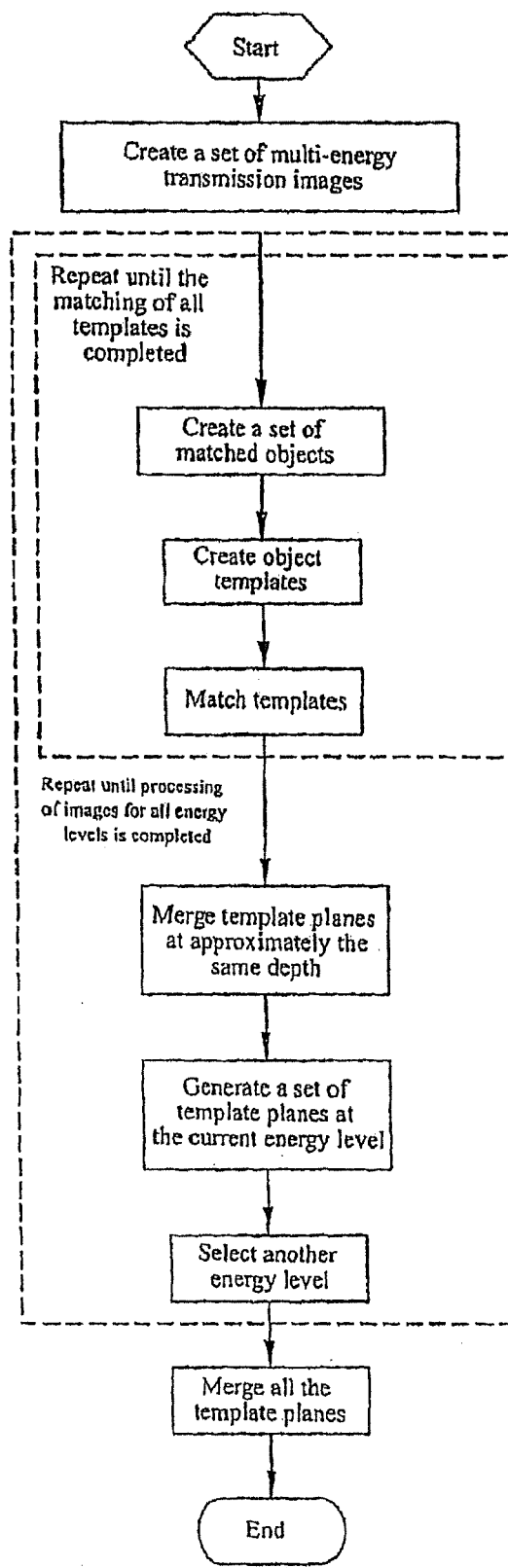
FIG. 4 shows a flow for obtaining a template image for each plane and energy according to the present invention.

FIG. 4 shows a flowchart of obtaining template planes for respective planes and energy levels according to the present invention. As shown in FIG. 4, a set is first created containing transmission images generated with respective levels of radiation energy. Next, a dual-loop operation with a nest of inner and outer loops is executed, the inner and outer dashed overlaps representing the two loops respectively. The inner loop serves to generate template planes. In this loop, a set of matched objects are first built. Then, template creation, matching and parallax calculation are applied to the objects in the binocular steroscopic transmission images for certain level of energy through the above steps 01 to 03, with the serial numbers of the matched objects being a loop variable. The templates with approximate parallax are merged into a single depth plane through logic operation "OR" so as to acquire a set of template planes of matched objects at respective depth planes for the certain level of radiation energy. The outer loop addresses different levels of radiation energy. This loop proceeds in the order of executing the inner loop, generating for the current energy a depth plane containing the templates of the matched objects at respective transmission depths, selecting the transmission images generated at next level of energy and repeating the preceding operations on the images, until the transmission images for all energy levels have been processed. After the completion of the outer loop, the sets of the template planes for different energy levels are combined through logic operation "OR" into a set of template planes each containing several object templates and using its depth as a discrimination mark.

2. Implementing Grey Reconstruction for Different Energy Levels According to the Depth Plane Templates.

The template planes obtained above reflect only the geometric shape of the objects and their positions in, for example, a freight container. The grey reconstruction for different energy levels is required to realize material identification. Through the grey reconstruction, the grey values at different energy levels can be obtained for each of the segmented objects. Then, the material identification can be implemented for these objects.

During the grey reconstruction, the grey values of the objects in each depth plane are reconstructed for each energy level through a binocular stereoscopic grey reconstruction method, in which the grey values are peeled off plane by plane from the outermost to the innermost. In other words, the grey reconstruction is first performed for the matched object at the outermost plane (immediately adjacent to the background region) in x-O-y plane. As a result, a reconstructed grey image of the object is obtained. In the reconstructed grey image, the background region has the same grey value with the original background, while the grey value inside the contour of the object become a value equal to the one obtained through an independent scanning on the object. Then, this object is peeled off from the original image by use of the reconstructed grey value. The same processing is then applied to the object at the next outermost plane. Such process is repeated until all of the matched objects have been subjected to the grey reconstruction.

Below the grey reconstruction is described in connection with the template images shown in FIG. 4, taking the left view in FIG. 5(a) as an example.

Figure 5:
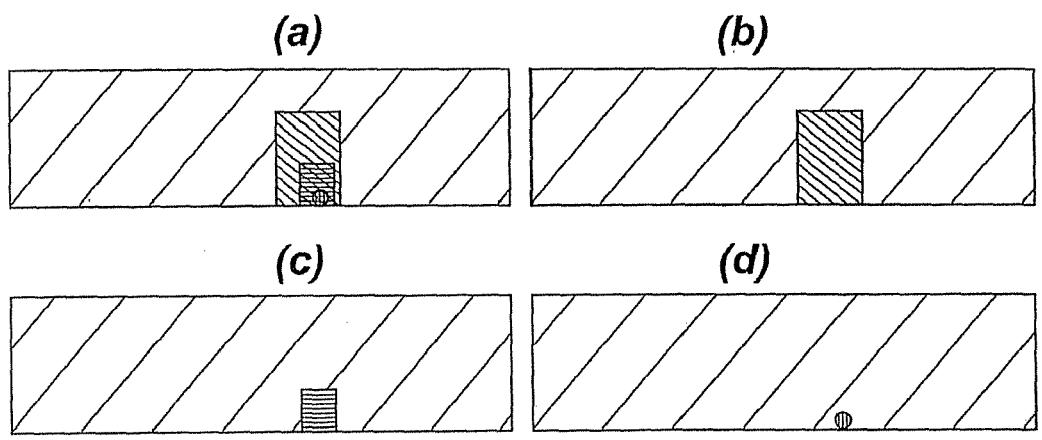
FIG. 5 shows an example of a left view and its grey reconstruction obtained by the method according to the present invention.

Referring to FIG. 5(a), three objects overlapping on each other are shown as a large rectangle, a small rectangle and a small ellipse from the outermost to the innermost. FIGS. 5(b), 5(c) and 5(d) show the effect of the grey reconstruction, in which FIG. 5(b) corresponds to the outermost plane, FIG. 5(c) to the middle and FIG. 5(d) to the innermost.

FIG. 5(b) shows the grey reconstruction result of the outermost object, in which the grey value of a light color region equals to that of the background region in the original image, and the grey value of a dark color region is obtained by subtracting the reconstructed grey value of the outermost object from the grey value of the light color region. As shown in the figure, the contour of the dark color region is a large rectangle identical to that of the object in its template image. FIG. 5(c) shows the grey reconstruction result of the middle object, in which the grey value of a light color region equals to that of the background region in the original image, and the grey value of a dark color region is obtained by subtracting the reconstructed grey value of the middle object from the grey value of the light color region. As shown in the figure, the contour of the dark color region is a small rectangle identical to that of the object in its template image. FIG. 5(d) shows the grey reconstruction result of the innermost object, in which the grey value of a light color region equals to that of the background region in the original image, and the grey value of a dark color region is obtained by subtracting the reconstructed grey value of the innermost object from the grey value of the light color region. As shown in the figure, the contour of the dark color region is a small ellipse identical to that of the object in its template image.

Figure 6:
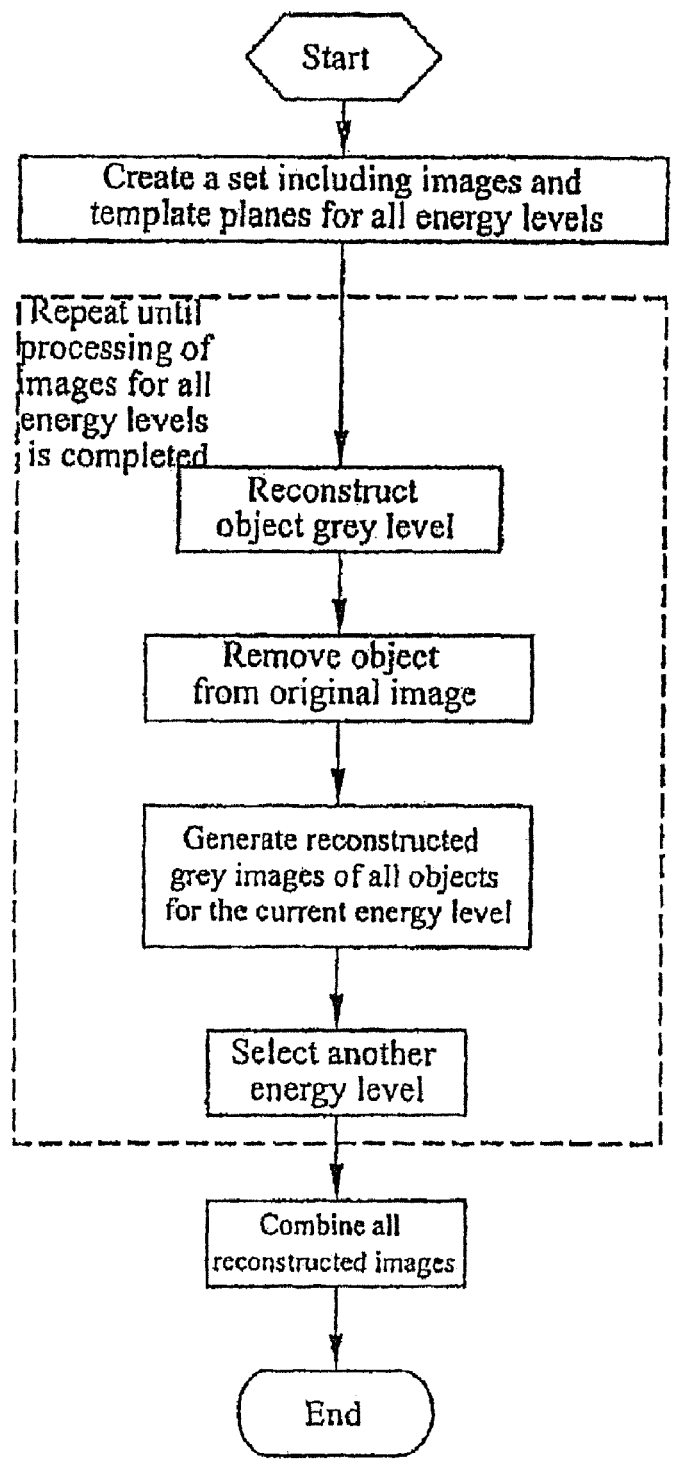
FIG. 6 shows a flow for grey reconstruction of grey images of different energy levels according to the present invention.

FIG. 6 shows a flow for grey reconstruction of grey images for different energy levels.

As shown in FIG. 6, the dashed block denotes a loop regarding different energy levels. First, a set is created containing the transmission images and the template depth plane set obtained through the first section of the implementation process. As mentioned above, the transmission images are obtained at different levels of radiation energy and distinguished from each other by energy levels, and the template depth plane set contains several object templates for each depth plane, with the transmission depth being the discrimination mark for these template planes. The grey image reconstruction for each energy level is completed in one loop, where the binocular steroscopic transmission image for this energy level is subjected to grey reconstruction, removal of an object from the original image and generation of a reconstruction grey image for the object, based on the result of the image segmentation in the first section of the overall process, i.e., the set of template planes obtained in the first section, and the details about the grey reconstruction will be given with reference to FIG. 7. Subsequently, the transmission image corresponding to another energy level is selected and subjected to the above steps, also based on the result of the image segmentation in the first section of the overall process. Such operation is repeated continuously, until all of the energy levels have been addressed. Finally, the reconstructed grey images of the objects for all the energy levels are combined into a set for use in material identification. This set can be, but not limited to, a ternary set including three nests. The first nest is a depth plane set including all the template planes discriminated from each other by transmission depth. The second nest is an object set including the matched objects at certain transmission depth, where these objects are discriminated from each other by their serial numbers. The third nest is an energy set including the reconstructed grey images of certain matched object at all the energy levels, where these images are discriminated from each other by different levels of radiation energy.

The above method for generating the reconstructed grey image of an object and completing the grey image reconstruction for each energy level is performed by peeling off each grey image plane by plane from the outermost to the innermost. In particularly, the grey value for the matched object on the outermost lay (directly adjacent to the background region) is first reconstructed and peeled off from the image. Then, the object on the second outermost lay is processed in the same way. This procedure is repeated until the grey value reconstruction has been performed on all the matched objects. The flow is shown in FIG. 7.

Figure 7:
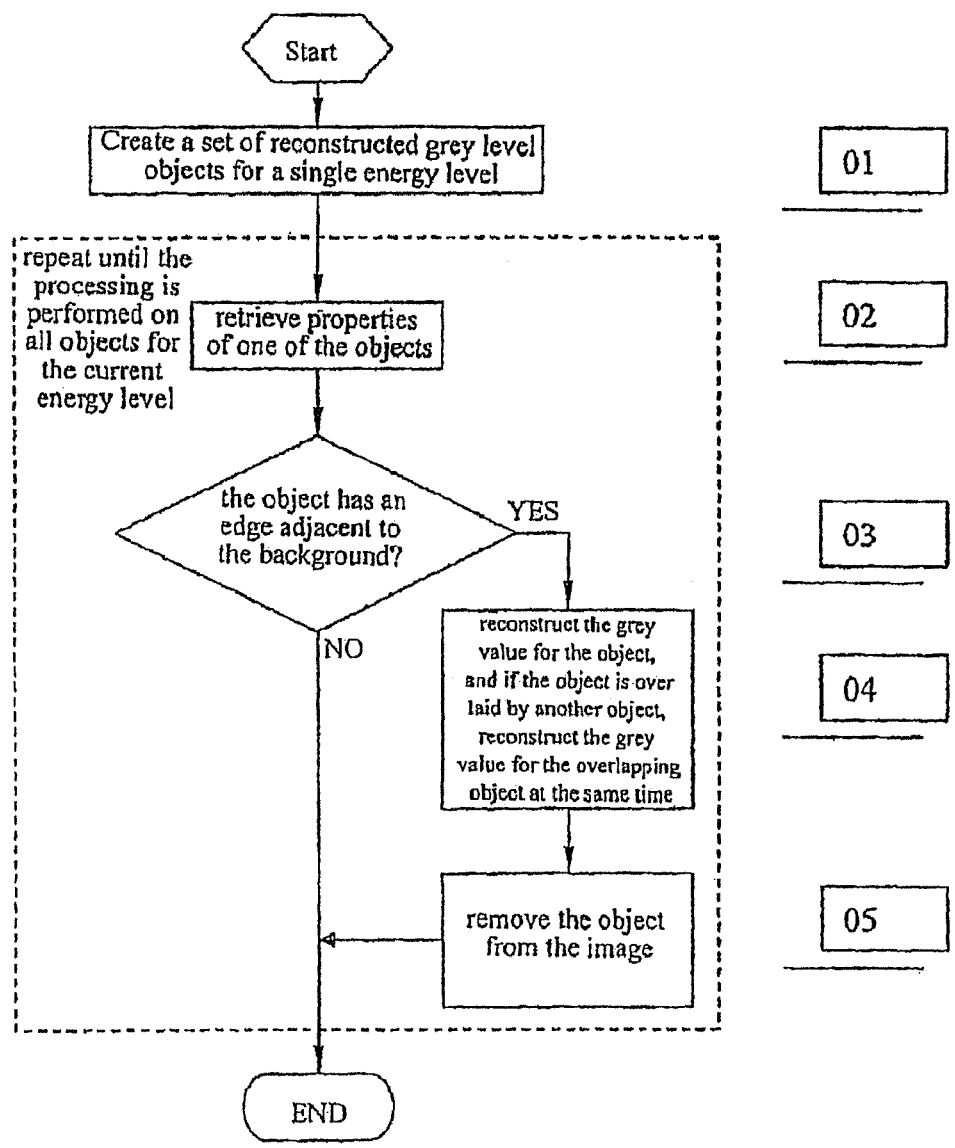
FIG. 7 shows a detailed flow for single-energy grey reconstruction according to the present invention.

FIG. 7 shows a detailed flow for single-energy grey reconstruction according to the present invention. Below the details about the grey reconstruction in the present invention will be given with reference to FIG. 7.

In the present invention, the grey value for each object is reconstructed by peeling off the grey value plane by plane from the outermost to the innermost. In particularly, the grey value for the matched object on the outermost lay (directly adjacent to the background region) is first reconstructed and peeled off from the image. Then, the object on the second outermost lay is processed in the same way. This procedure is repeated until the grey value reconstruction has been performed on all the matched objects. The specific flow is:

step 01: establishing a candidate object set for grey value reconstruction by using the objects obtained from the image segmentation process;

step 02: retrieving the properties of one of the objects;

step 03: determining whether the retrieved object has an edge adjacent to the background region;

step 04: reconstructing the grey value for the object if the retrieved object has an edge adjacent to the background region, and, if the object is overlaid by another object, reconstructing the grey value for the overlaying object;

step 05: removing the object from the image.

For each object in the object set, the steps 02 to 05 are repeated until the grey value reconstruction has been performed on all the matched objects.

During the process of grey value reconstruction, each of the objects comprises only two types of parts, one being the part adjacent to the background region, the other being the part overlaid by another object. For an object which is initially overlaid completely and thus has no edge adjacent to the background, some of the region where the overlapping object lies must turn into part of the background region and thus can be treated as a new background region after a sufficient number of peeling off, and therefore the overlaid object will has an edge adjacent to the background region. The reconstructed grey value for the object equals to the difference between the grey value outside the edge and that inside the edge, that is, $$S_{obj} = (S_{out} - S_{in})$$

3. Performing Material Identification on the Reconstructed Template Planes for Any Object in the Planes The grey values at different energy levels can be obtained for any of the objects represented by each template at each plane, after the above grey reconstruction. The grey values vary with different energy levels, and material identification can be made to the objects at any of the planes by analyzing such variation.

Figure 8:
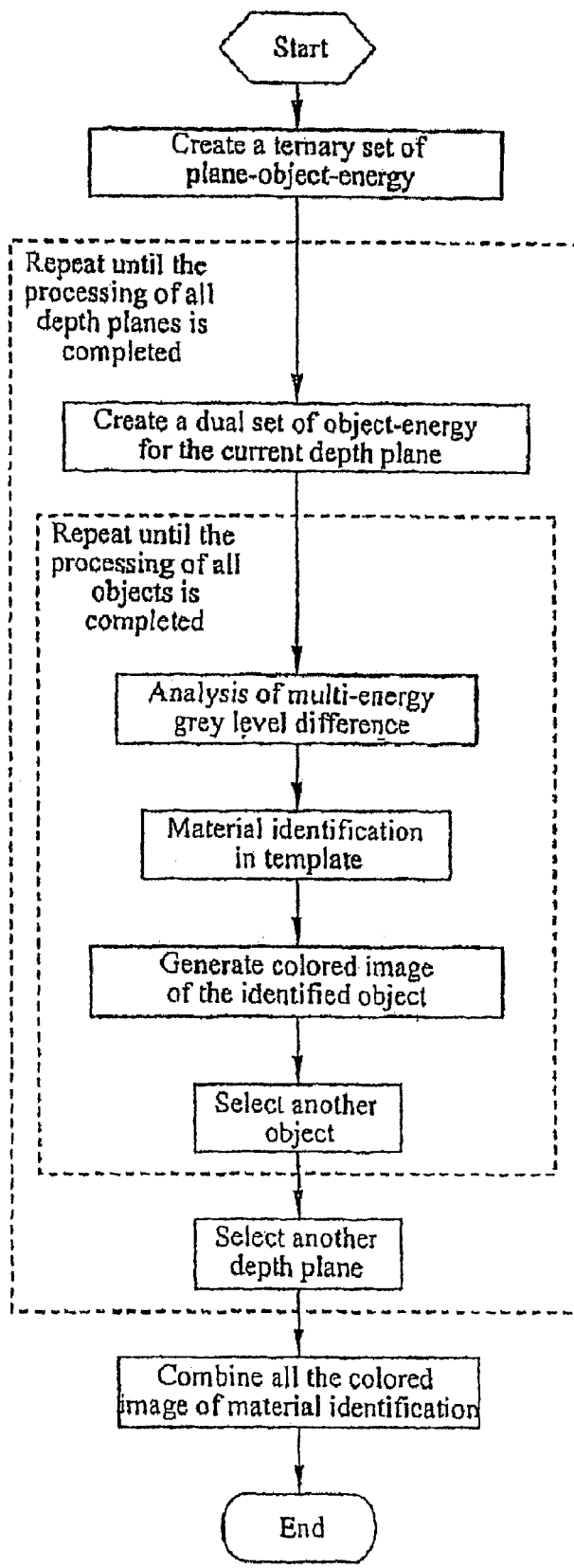
FIG. 8 shows a flowchart of material identification of an object at any plane according to the present invention.

FIG. 8 shows the flow of the material identification. Referring to FIG. 8, the ternary set of "plane-object-energy" is first introduced from the second section of the implementation process. Next, a dual loop of "plane-object" is executed, where the outer dashed block denotes a loop regarding each transmission depth. In this outer loop, a dual set of "object-energy" is created for each transmission depth, where the dual set includes the matched objects at the plane and the reconstructed grey images of each object at all the energy levels. Then, the flow proceeds to the object loop denoted by the inner dashed block. The inner loop is executed for all the matched objects at certain depth plane, with the serial number of each object being the loop variable. Subsequently, each of the objects at the current depth plane, that have been matched between the left and right views and undergone grey reconstruction for all the energy levels, is subjected sequentially to analysis of grey difference, material identification and generation of colored image (this processing procedure has been elaborated in "DESCRIPTION OF PRIOR ART" of Patent Publication CN 1995993 of the applicant, thus no detail will be repeated here.). After the identification of material properties of all the objects is completed for the current depth plane, a colored depth plane is drawn in the depth plane marked by the current plane depth, according to the template planes obtained from the first section of the overall process, the reconstructed grey images obtained from the second section and the result of identification obtained above. In such colored depth plane, the contour of each identified object is determined by the template contour, and the color filled in the contour is determined by both of the results of grey reconstruction and material identification. How to determine the color will be described in connection with FIG. 9. Next, a new set of "object-energy" is also created for another depth plane, which is followed by material identification and colored image reconstruction. Such process is repeated until all the depth planes have undergone the above processing. After that, all the resultant colored template planes exhibiting the effect of material identification are combined in the order of the depth planes into a set containing all the colored template planes exhibiting the effect of material identification for respective objects at the different transmission depth. This set is the final result obtained through the binocular steroscopic and multi-energy image processing technique according to the present invention.

For non-overlapping objects, the multi-energy material identification method can identify the material of any object according the grey difference between transmission images at different energy levels. The colors are defined, but not limited to, such that orange is used as identification color for organic or light material, green for light metal or mixture, blue for metal. Also, whether each color is lighter or darker depends on the magnitude of the reconstructed grey value. The identification effect is achieved as shown in FIG. 9.

Figure 9:
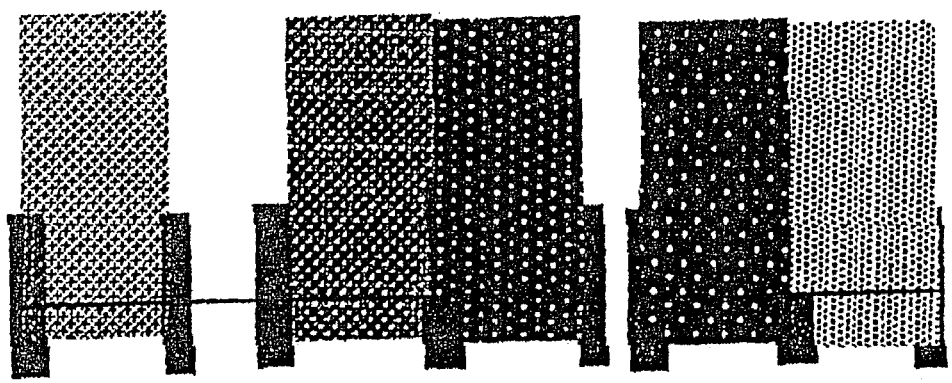
FIG. 9 is a diagram showing the effect of multi-energy identification for various types of non-overlapping materials.

With reference to FIG. 9, the multi-energy identification effect is shown as rectangular for graphite, aluminum, iron, lead and polyethylene in the case of mass thickness 30 g/cm$^2$.

In FIG. 9, the identification targets are arranged from left to right as graphite, aluminum, iron, lead and polyethylene, and the identification colors are orange, green, blue, blue and orange, respectively. Thus, no error occurs in material identification.

Figure 10:
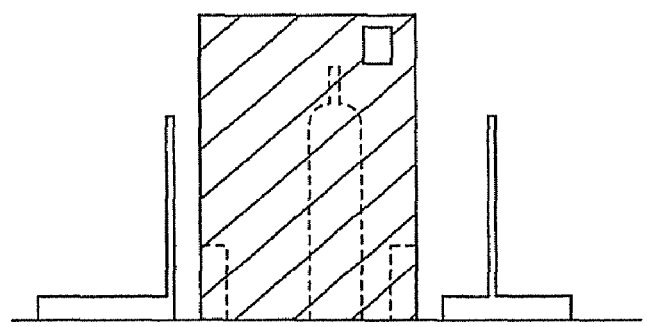
FIG. 10 is a diagram showing the effect of identification without peel-off processing.

In the case that the objects overlap on each other, the identification may be incorrect if no peel-off processing is made on the overlapped parts. FIG. 10 is a diagram showing the effect of identification without peel-off processing.

As show in FIG. 10, a large rectangular steel sheet overlaps a steel container filled with liquefied petroleum gas in the middle, a paper box filled with CDs on the left and a paper box filled with cigarettes on the right. The results of the identification regarding the liquefied petroleum gas in the steel container and the cigarettes in the paper box on the right side are incorrect, and the result of the identification regarding the CDs in the paper box is partially wrong.

Figure 11:
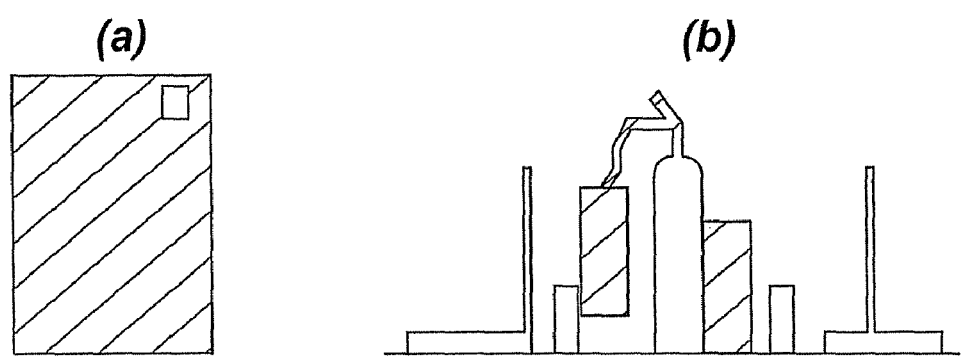
FIG. 11 is a diagram showing the effect of multi-energy material identification with binocular steroscopic peel-off processing on unwanted obstacles.

In contrast, FIG. 11 shows the effect of multi-energy material identification with binocular steroscopic peel-off processing on unwanted obstacles, where FIG. 11(a) shows the overlapping object, and FIG. 11(b) shows the identified object.

As which can be seen from FIG. 11, by applying the multi-energy material identification with binocular steroscopic peel-off processing on unwanted obstacles, the overlapping steel sheet is identified as blue representing metal in FIG. 11(a), and the CDs in the paper box, the liquefied petroleum gas and the cigarettes in the paper box are identified as orange representing organic, as shown in FIG. 11(b). The identification results are all correct.

Figure 12:
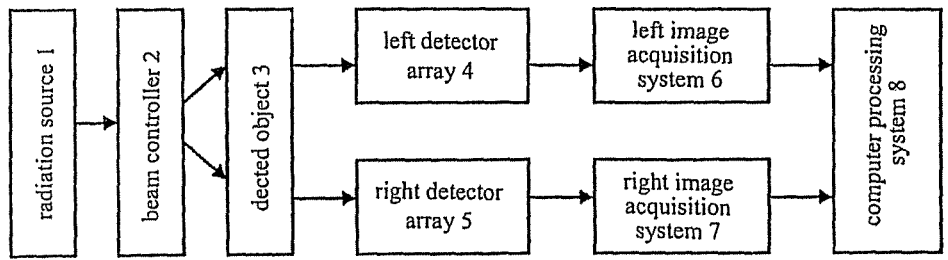
FIG. 12 is a diagraph showing the architecture of a binocular stereoscopic and multi-energy scanning radiographic imaging system.

FIG. 12 is a diagram showing the architecture of a binocular stereoscopic and multi-energy scanning radiographic imaging system according to the present invention. As shown in FIG. 12, the binocular stereoscopic and multi-energy scanning radiographic imaging system according to the present invention comprises:

a multi-energy radiation source 1 which is an X-ray generator for generating X-rays of different energy levels;

a beam controller 2 which receives the X-rays emitted by the radiation source 1 and generates two beams of X-rays which are symmetric or asymmetric and have an angle between them;

a left detector array 4 which receives the X-rays of different energy levels and converts them into electric signals to be inputted to a left image acquisition system 6;

a right detector array 5 which receives the X-rays of different energy levels and converts them into electric signals to be inputted to a right image acquisition system 7;

the left image acquisition system 6 which receives the electric signals sent by the left detector array 4 and acquires left image data from the electric signals;

the right image acquisition system 7 which receives the electric signals sent by the right detector array 5 and acquires right image data from the electric signals;

a computer processing system 8 which receives the left and right image data from the left and right image acquisition systems 6 and 7 respectively, processes the left and right image data and displays the image of the object under detection on the computer display as well as the depth plane transmission images at different depths reconstructed from the image data.

In the present invention, the radiation source 1, cooperating with the beam is controller 2, emits two beams of X-rays, which are symmetric or asymmetric and have an angle between them. The X-rays, after penetrating through an object under detection 3, are received by the left detector array 4 and the right detector array 5, respectively, and then converted into electric signals to be inputted to the left and right image acquisition systems 6 and 7, respectively. Having been processed by the computer processing system 8, the image data from the left and right image acquisition systems 6 and 7 can be used to display the image of the object under detection on the computer display as well as the depth plane transmission images at different depths reconstructed from the image data.

To the binocular stereoscopic images at each of the different energy levels, the binocular stereoscopic and multi-energy scanning radiographic imaging system according to the present invention can apply binocular stereoscopic processing technique to obtain the template depth planes of transmission images for this energy level, merge the template depth planes for the different energy levels into a set of template depth plane images. Then, based on the template depth plane images, the system performs the grey reconstruction for the multiple energy levels, respectively, and identifies the material at each depth plane for the reconstructed depth plane images. The specific operation and process are the same as described for the binocular stereoscopic and multi-energy scanning radiographic imaging method, and the detailed description is not repeated here.

Figure 13A:
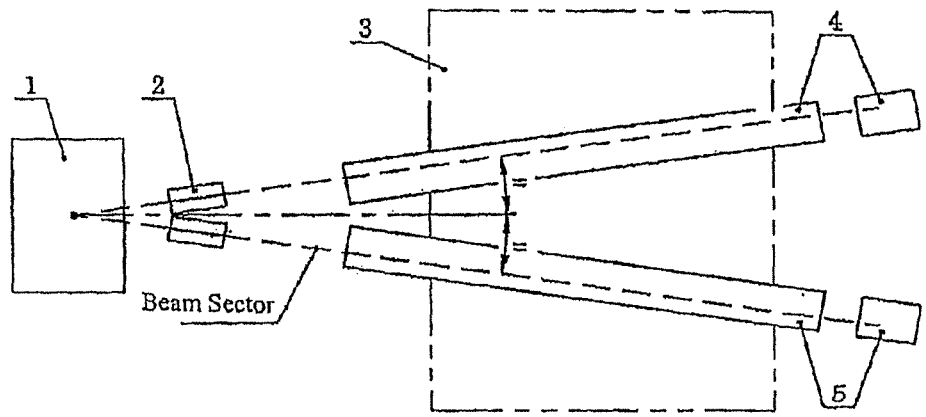
FIGS. 13A and 13B are plan views showing a case of symmetric ray beams and asymmetric ray beams, respectively.
Figure 13B:
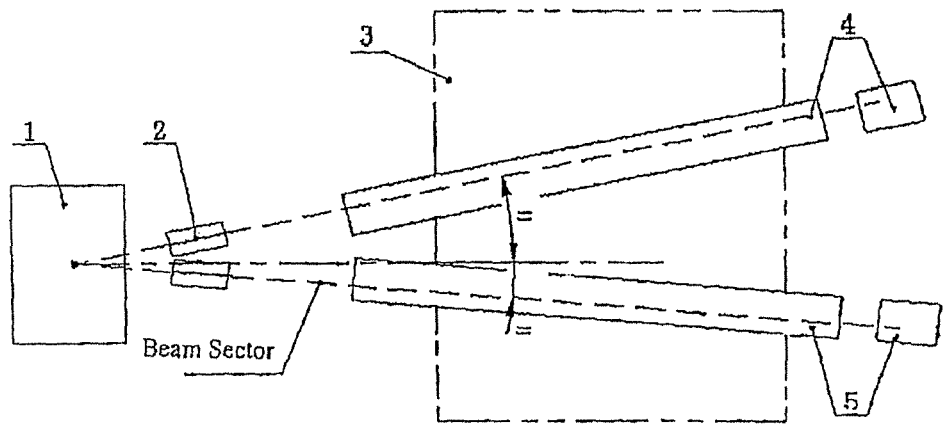
Figure 14:
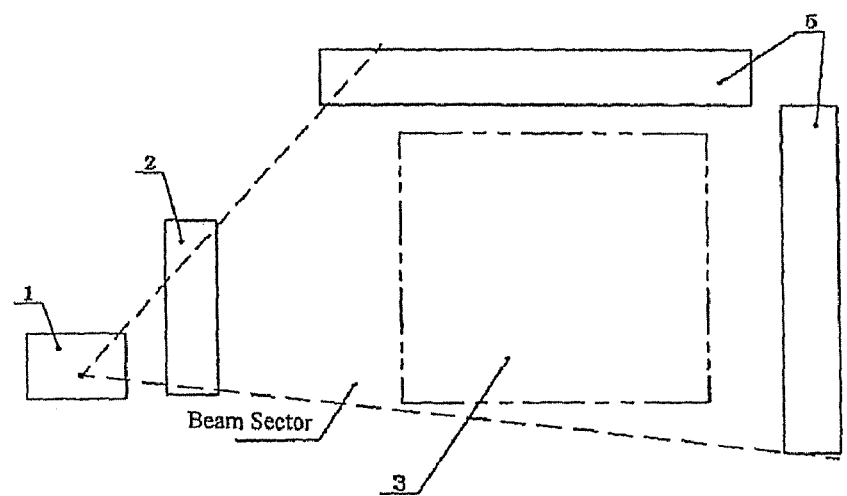
FIG. 14 is a side view of the binocular stereoscopic and multi-energy scanning radiographic imaging system.

FIGS. 13 and 14 are plan and side views for schematic layout of the devices needed for implementing the present invention, respectively, where FIG. 13A depicts the case of symmetric ray beams, and FIG. 13B depicts the case of asymmetric ray beams. As shown in FIGS. 13 and 14, two collimation slits are provided in the beam controller to shape the X rays emitted by the radiation source into two ray beams, either symmetric or asymmetric, with an angle between them. Both of the left detector arrays 4 and 5 face directly the beam sector defined by the collimation slits of the double-slit collimator, scan and examine the object under detection in a symmetric fashion and transmit the electric signals to the corresponding left and right image acquisition systems. Then, the computer processing system 8 carries out image processing to obtain the transmission images of depth plane containing depth information.

As described in the above example, the method of the present invention can enable material identification, along the ray direction, not only on the dominant components but also on the non-dominant components in transmission images, by peeling off the dominant components. The conventional multi-energy material identification method can identify only the material of dominant components along the ray direction. For example, in the case that a thick steel sheet overlaps on a small bag of drug along the ray direction, the conventional multi-energy material identification method can only identify the steel sheet along the ray direction, without any result regarding the drug. With the method of the present invention, the steel sheet and the drug are first divided to two different depth planes through the binocular steroscopic technique. Then, the multi-energy grey reconstruction is applied to each plane, so that material identification can be made plane by plane. As such, both the steel sheet (dominant component contributing a large amount of ray attenuation along the ray direction) and the drug (non-dominant component contributing a small amount of ray attenuation along the ray direction) can be identified. The method of the present invention is particularly useful in material identification for transmission images of a freight container. In the transmission images of a freight container, harmful objects, such as explosive and drug, are usually non-dominant components along the ray direction, due to the size of the freight container and the long distance of ray penetration. Therefore, the method lays a fundament for automatic identification of harmful objects, such as explosive, drugs, etc., from the scanning transmission images of the freight container.

What is claimed is:

1. A material identification and imaging method using binocular steroscopic and multi-energy transmission images comprise the following steps:
   1) causing two angled X-ray beams to penetrate through objects under examination so as to obtain data of left and right transmission images, segmenting said left and right transmission images and matching the results of said segmentation;
   2) creating a depth plane along the depth direction of the transmission images;
   3) repeating the above process on transmission images of variation energy to obtain a depth plane of each depth plane for the variation energy;
   4) merging the depth planes for different energy levels at the same position to obtain a depth plane for each depth plane and energy of a predetermined group of energy levels;
   5) identifying the material of the objects for each of which a grey reconstruction in said depth plane succeeds.

2. The method of claim 1, wherein the segmentation of said left and right transmission images in the step 1) is implemented according to an edge extraction algorithm.

3. The method of claim 1, wherein the segmentation of said left and right transmission images in the step 1) further comprises steps of:
   1) extracting edges in each of the said left and right transmission images;
   2) obtaining enclosed edges in these images; and
   3) segmenting these images according to the obtained enclosed edges.

4. The method of claim 1, wherein the matching of the results of said segmentation in the step 1) is implemented according to the geometric characteristics of the left and right segmentation results.

5. The method of claim 1, wherein the matching of the results of said segmentation in the step 1 further comprises steps of:
   1) creating objects for the segmentation results;
   2) allocating corresponding weights to the property set of the objects.

6. The method of claim 1, wherein the creating in the step 2) is implemented based on a matched result of the left and right images as well as the corresponding absolute parallax.

7. The method of claim 1, wherein a reconstruction of grey value for template planes is implemented by peeling off grey value plane by plane from the outermost to the innermost, in particular, a grey value for the matched object on the outermost lay immediately adjacent to the background region is first reconstructed and peeled off from the image, the object on the second outermost lay is then processed in the same way, and this procedure is repeated until the grey value reconstruction has been performed on all of the matched objects.

8. The method of claim 1, includes reconstructing of a grey value for template planes comprises steps of:
   1) establishing a candidate object set for grey value reconstruction by using objects;
   2) retrieving properties of one of said objects;
   3) determining whether the retrieved object has an edge adjacent to the background;
   4) reconstructing the grey value for the object if the retrieved object has an edge adjacent to the background, and, if the object is overlaid by another object, reconstructing the grey value for the overlapping object as well;
   5) removing the object from the image;
   and for each object in the object set, the steps 2) to 5) are repeated until the grey value reconstruction has been performed on all of the matched objects.

9. The method of claim 3, wherein said edge extraction in the image is conducted by using Sobel and Canny edge detection operator simultaneously.

10. The method of claim 9, wherein, for each pixel in an digital image $\{f(i,j)\}$, said Sobel edge detection operator calculates a weighted grey difference between the pixel and its neighbor pixels, with the nearer neighbor pixel having a larger weight and the farther neighbor pixel having a smaller weight.

11. The method of claim 9, wherein the edge extraction by using said Canny edge detection operator comprises steps of:
1) smoothing an image with a Gauss filter;
2) calculating the magnitude and direction of gradient by use of finite difference of one-order partial derivative;
3) applying non-maximum suppression to the magnitude of gradient; and
4) detecting and connecting edges via a double threshold algorithm.

12. The method of claim 4, includes obtaining of enclosed edges such that two edge pixels are connected based on the similarity between them in terms of gradient magnitude or gradient direction.

13. The method of claim 8, wherein the grey value is reconstructed for the object retrieved in the step 3) if the object has an edge adjacent to the background, and, if the object is overlaid by another object, the grey value is reconstructed at the same time for the overlapping object; then, the object is removed from the object set and the image.

14. The method of claim 1, further comprising:
performing grey reconstruction, object removal from the original image and generation of reconstructed grey images of each object with respect to the binocular stereoscopic transmission images for one energy level, so as to complete the grey image reconstruction for one energy level; and
selecting another energy level to repeat the steps of grey image reconstruction, and finally combining the reconstructed grey images of the object for all the energy levels into one set.

15. The method of claim 1, wherein the identifying in step 5) further comprises:
performing sequentially analysis of grey difference, material identification and generation of colored image on each of the objects for which the left and right views have been matched and the grey reconstruction for all the energy levels has been completed; and
combining the processing results of all the objects in order of depth planes into a set of identification effect images for the objects at each of the depth planes.

16. A binocular stereoscopic and multi-energy scanning radiographic imaging system comprising a radiation source, a left detector array, a right detector array, a left image acquisition system, a right image acquisition system and a computer processing system, wherein:
said radiation source is an X-ray generator for generating X-rays of different energy levels;
said left detector array receives the X-rays of different energy levels and converts them into electric signals to be inputted to said left image acquisition system;
said right detector array receives the X-rays of different energy levels and converts them into electric signals to be inputted to said right image acquisition system;
said left image acquisition system receives the electric signals sent by said left detector array and acquires left image data from the electric signals;
said right image acquisition system receives the electric signals sent by said right detector array and acquires right image data from the electric signals; and
said computer processing system receives said left and right image data from the left and right image acquisition systems respectively, processes said left and right image data at different energy levels to identify the material of an object at a specific depth plane wherein:
said computer processing system segments said left and right image data at different energy levels and matches the results of said segmentation so as to create depth planes of transmission images of the different energy levels in the depth direction, reconstructs grey values of the depth planes to obtain a depth plane of each depth plane for each different energy level, merges the depth planes for different energy levels at the same position to obtain a depth plane for each depth plane and energy of a predetermined group of energy levels, and identifies the material of each matched object in each depth plane.

17. The scanning radiographic imaging system of claim 16, further comprising:
a beam controller for receiving the X-rays emitted by the radiation source and generating two beams of X-rays which are symmetric or asymmetric and have an angle between them.

18. The scanning radiographic imaging system of claim 17, wherein said beam controller is a double-slit collimator.

19. The scanning radiographic imaging system of claim 18, wherein two collimation slits are provided in said double-slit collimator to shape the X-rays emitted by said radiation source into two beam sector, either symmetric or asymmetric, with an angle between them.

20. The scanning radiographic imaging system of claim 16, wherein said detector arrays comprises "L"-type arranged detectors.

21. The scanning radiographic imaging system of claim 16, wherein said
computer processing system can also display the images of the objects under detection, respectively, based on the left and right image data.

* * * * *